(12) United States Patent
Zhang et al.

(10) Patent No.: US 10,799,379 B2
(45) Date of Patent: Oct. 13, 2020

(54) DELIVERY SYSTEM AND LUMEN STENT SYSTEM

(71) Applicant: Lifetech Scientific (Shenzhen) Co., Ltd., Shenzhen (CN)

(72) Inventors: Junqiang Zhang, Shenzhen (CN); Gang Wang, Shenzhen (CN); Chengmei Guan, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 168 days.

(21) Appl. No.: 16/063,270

(22) PCT Filed: Jun. 14, 2016

(86) PCT No.: PCT/CN2016/085718
§ 371 (c)(1),
(2) Date: Jun. 16, 2018

(87) PCT Pub. No.: WO2017/113626
PCT Pub. Date: Jul. 6, 2017

(65) Prior Publication Data
US 2018/0369006 A1    Dec. 27, 2018

(30) Foreign Application Priority Data
Dec. 28, 2015 (CN) .......................... 2015 1 1006212

(51) Int. Cl.
*A61F 2/966* (2013.01)
*A61F 2/07* (2013.01)
*A61F 2/95* (2013.01)

(52) U.S. Cl.
CPC ............... *A61F 2/966* (2013.01); *A61F 2/07* (2013.01); *A61F 2/9517* (2020.05); *A61F 2/9522* (2020.05); *A61F 2002/9665* (2013.01)

(58) Field of Classification Search
CPC ...... A61F 2002/9522; A61F 2002/9665; A61F 2/95
See application file for complete search history.

(56) References Cited

U.S. PATENT DOCUMENTS 6,077,297 A    6/2000 Robinson et al.
6,214,036 B1 *    4/2001 Letendre .................. A61F 2/07
                                                                      623/1.11
(Continued)

FOREIGN PATENT DOCUMENTS

| CN | 101415377 A | 4/2009 |
| CN | 105007865 A | 10/2015 |
| EP | 2745811 A1 | 6/2014 |

OTHER PUBLICATIONS

International Search Report dated Sep. 26, 2016 for corresponding PCT Application No. PCT/CN2016/085718.
(Continued)

*Primary Examiner* — Alexander J Orkin
(74) *Attorney, Agent, or Firm* — Raymond Sun

(57) ABSTRACT

A delivery system (200) for delivering a lumen stent (100). The delivery system (200) comprises a fixing anchor (270) and a fixing cap (260) which is cylindrical and has an opening at a proximal end, the fixing anchor (270) comprising a hollow insertion part (271) and an abutment part (273) connected to the insertion part (271); parts of the side surface of the insertion part (271) are recessed towards the interior of the insertion part (271) to form a plurality of positioning grooves (2711) that extend to a proximal end surface of the insertion part (271), a separator (2713) being formed between every adjacent two positioning grooves (2711); the abutment part (273) comprises a carrier (2731) and a plurality of first position-limiting pieces (2733) provided on a side of the carrier (2731), a distal end of each first position-limiting piece (2733) being provided to correspond (Continued)

to an open side of a positioning groove (2711) adjacent to the abutment part (273); distal end surfaces of the plurality of first position-limiting pieces (2733), a distal end surface of the carrier (2731) and proximal end surfaces of the separators (2713) are coplanar. When the fixing anchor (270) and the fixing cap (260) are joined, the insertion part (271) is inserted into the fixing cap (260), and the distal end surfaces of the first position-limiting pieces (2733) abut the proximal end surface of the fixing cap (260). Further disclosed is a lumen stent system. The delivery system (200) can be smoothly and safely withdrawn out of the human body.

19 Claims, 7 Drawing Sheets

(56) References Cited

U.S. PATENT DOCUMENTS

| | | | | |
|---|---|---|---|---|
| 2003/0114880 A1* | 6/2003 | Hansen | ............... | A61F 2/013 606/200 |
| 2004/0267348 A1* | 12/2004 | Gunderson | ............... | A61F 2/91 623/1.12 |
| 2005/0049667 A1* | 3/2005 | Arbefeuille | ............... | A61F 2/07 623/1.11 |
| 2007/0043420 A1* | 2/2007 | Lostetter | ............... | A61F 2/95 623/1.11 |
| 2008/0114443 A1* | 5/2008 | Mitchell | ............... | A61F 2/07 623/1.13 |
| 2009/0287290 A1* | 11/2009 | Macaulay | ............... | A61F 2/2436 623/1.11 |
| 2011/0257720 A1 | 10/2011 | Peterson et al. | | |
| 2012/0078350 A1* | 3/2012 | Wang | ............... | A61F 2/2436 623/2.11 |
| 2012/0245606 A1* | 9/2012 | Goldberg | ............... | A61F 2/0036 606/153 |
| 2013/0274860 A1* | 10/2013 | Argentine | ............... | A61F 2/9517 623/1.12 |
| 2013/0289698 A1* | 10/2013 | Wang | ............... | A61F 2/2436 623/1.12 |
| 2014/0215790 A1* | 8/2014 | Soundararajan | ............... | A61F 2/95 29/428 |
| 2014/0236278 A1* | 8/2014 | Argentine | ............... | A61F 2/962 623/1.12 |
| 2014/0350656 A1 | 11/2014 | Zacharias et al. | | |

OTHER PUBLICATIONS

Office Action dated Dec. 13, 2017 for corresponding China Application No. 201511006212.1.

* cited by examiner

DELIVERY SYSTEM AND LUMEN STENT SYSTEM

TECHNICAL FIELD

The present disclosure relates to the technical field of medical devices, and more particularly relates to a delivery system and a lumen stent system.

BACKGROUND ART

Aortas of a human body include an ascending aorta, an aortic arch, a thoracic descending aorta and an abdominal aorta. As various pathologic changes, such as inflammation and anabrosis, will cause injury to endangium or vascular walls of the aortas, diseases such as an arterial aneurysm is liable to occur under the combined action of blood flow impact. Once the arterial aneurysm is ruptured, blood would flow out of a blood vessel, leading to insufficient blood volume for blood circulation of a patient, which causes shock or death to the human body.

Therapies for arterial aneurysm diseases generally include a surgical therapy and a drug therapy. At the present time, surgical therapy is the main therapy. The conventional surgical therapy (namely an invasive operation) is a therapy to build an extracorporeal blood circulation, then cut off the arterial aneurysm diseased blood vessel, and connect the blood vessel with an artificial blood vessel to achieve a normal circulation of arterial blood. The conventional surgical therapy for treating the arterial aneurysm diseases is high in operational risk and may cause a significant trauma to the patient, and if such great trauma is caused to elderly or weak patients, it would take a relatively long time for them to recover from the operation.

Since the 1990s, an interventional therapy for treating aortic cardiovascular diseases has become the new therapy. With the continuous development of interventional technology, advantages of adopting a lumen stent to treat aortic aneurysm and aortic dissection diseases have been increasingly outstanding. An aorta lumen stent is an artificial lumen matched with the size of a lumen, and it can be used according to the following steps: first, the lumen stent is compressed into a sheath of a delivery system; second, the blood vessel is punctured at the position of the femoral artery or the iliac artery, and then a track is built with a guide wire; third, the delivery system loaded with the lumen stent is delivered to the diseased position through the iliac artery, the abdominal aorta, the thoracic aorta, the aortic arch and the ascending aorta; fourth, the lumen stent is released and expands to abut against the arterial aneurysm wall, and a membrane which is overlaid on the lumen stent isolates blood flow from the diseased part, thereby eliminating the impact of the blood flow to the arterial aneurysm wall of the diseased part and building a normal blood circulation channel; and finally, the guide wire and the delivery system are withdrawn to complete the interventional treatment of arterial aneurysms and aortic dissections.

With high blood flow pressure and high impact, blood in the aortic blood vessel impacts the lumen stent when it is being released, so that there is a risk that the lumen stent can move; and therefore, in recent years, a lumen stent with connection parts has been introduced, and in the releasing process of the lumen stent, the connection parts are fixed in the delivery system all the time, so that no movement can occur during the releasing process; and the releasing of the lumen stent is completed before the connection parts are separated from the delivery system.

However, after the releasing of the lumen stent with connection parts is completed, during withdrawal of the delivery system, it is easy for the delivery system to hook the released lumen stent, and more particularly, hook the connection parts of the lumen stent, which would result in movement of the lumen stent, and thereby result in the failure of the interventional operation, thus increasing the operation risk to the patients.

SUMMARY OF THE INVENTION

In light of the above, it is necessary to provide a lumen stent system which may enable a delivery system to be safely and successfully withdrawn after a lumen stent with connection parts has been completely released.

The present disclosure provides a delivery system for delivering a lumen stent. The delivery system includes a fixing anchor and a barrel-shaped fixing cap having a proximal end with an opening; the fixing anchor includes a hollow insertion part and an abutment part connected with the insertion part; part of the side surface of the insertion part is sunken towards the inside of the insertion part to form a plurality of positioning grooves penetrating through the proximal end surface of the insertion part; a separator is formed between every two adjacent positioning grooves; the abutment part includes a hollow carrier and a plurality of first position-limiting members arranged on the side surface of the carrier; the distal end of each first position-limiting piece is arranged to correspond to the open side, which is close to the abutment part, of one positioning groove; the distal end surfaces of the first position-limiting members, the distal end surface of the carrier and the proximal end surfaces of the separators are coplanar; and when the fixing anchor and the fixing cap are joined, the insertion part is inserted into the fixing cap, and the distal end surfaces of the first position-limiting members abut against the proximal end surface of the fixing cap.

In one embodiment, the abutment part also includes a plurality of second position-limiting members; the number of the second position-limiting members is equal to that of the first position-limiting members; the second position-limiting members and the first position-limiting members are alternately arrayed on the side surface of the carrier; each second position-limiting piece is arranged to correspond to a separator; and the distal end surface of each second position-limiting piece abuts against the proximal end surface of each corresponding separator.

In one embodiment, the width of the separators along the circumferential direction of the insertion part is greater than the corresponding second position-limiting members along the circumferential direction of the abutment part.

In one embodiment, the cross sections, which are perpendicular to the longitudinal central line of the fixing anchor, of the distal ends of the surfaces, far away from the carrier, of each first position-limiting piece and each second position-limiting piece are shaped like arc sections, and the diameters of the arc sections are equal to the outer diameter of the proximal end of the fixing cap.

In one embodiment, the lengthwise directions of the first position-limiting members and the second position-limiting members are all parallel to the longitudinal central line of the fixing anchor, and the proximal ends of the first position-limiting members and the second position-limiting members all extend towards the proximal end of the carrier; the lengths of the first position-limiting members and the second position-limiting members are all less than the axial length of the carrier; and the outer surfaces of the proximal ends of each first position-limiting piece and each second position-limiting piece are in smooth conical transition with the outer surface of the proximal end of the carrier.

In one embodiment, the side, which is far away from the abutment part along a direction of the longitudinal central line of the insertion part, of each positioning groove is a closed side.

In one embodiment, the delivery system further includes an inner core tube an end socket arranged at the distal end of the inner core tube, and an outer core tube which surrounds the inner core tube and may axially move relative to the inner core tube; the fixing cap is arranged at the proximal end of the end socket, and surrounds the inner core tube; the fixing anchor is arranged at the distal end of the outer core tube, and surrounds the outer core tube; and the fixing cap is closer to the end socket than the fixing anchor.

In one embodiment, the proximal end of the carrier extends to the outer core tube, and the outer surface of the proximal end of the carrier is in conical transition with the outer surface of the outer core tube.

The present disclosure further provides a lumen stent system, including a lumen stent and any above-mentioned delivery system. The lumen stent includes a bare stent; the bare stent includes waveform rings and a plurality of connection parts connected with the waveform rings; when the fixing anchor and the fixing cap are joined, the connection parts of the stent are received in the positioning grooves; a small hole is formed in a plane, where the proximal end surface of the fixing cap is located, by each separator, each first position-limiting piece adjacent to each corresponding separator, the fixing cap and the carrier; and the width of the small hole along the circumferential direction of the fixing anchor is less than that of the end portion of each connection part along the circumferential direction of the lumen stent.

In one embodiment, when the fixing anchor and the fixing cap are joined, the first position-limiting members are clamped with the crest parts of the waveform rings.

In one embodiment, the connection part is of a U-shaped open-loop structure with an opening in one side; the waveform ring is disconnected at the crest part; two ends of the open side of each connection part are respectively connected with two ends of each disconnected position of each waveform ring; axial backward movement limiting members are arranged in the positioning grooves of the insertion part; each axial backward movement limiting piece is spaced from the side, which is perpendicular to the circumferential direction of the insertion part, of each positioning groove, and protrudes from the groove bottom, which is parallel to the circumferential direction of the insertion part, of each positioning groove; the connection parts are received in the positioning grooves; and the connection parts are clamped with the axial backward movement limiting members.

In one embodiment, the axial backward movement limiting members extend towards the first position-limiting members along the longitudinal central line of the fixing anchor, and are connected with the first position-limiting members.

In one embodiment, barbs are arranged on the connection parts.

In the delivery system of the present disclosure, the distal end surface of the first position-limiting members, the distal end surface of the carrier and the proximal end surface of the separator are coplanar, so that when the fixing anchor and the fixing cap are joined, the end surface of the fixing cap, which abuts against the fixing anchor, is divided into a plurality of small holes by the first position-limiting members, the carrier and the separator to prevent the delivery system from hooking the released lumen stent when withdrawn.

DETAILED DESCRIPTION OF THE INVENTION

For the purpose of making the understanding of objects, technical features and effects of the present disclosure clearer, a further detailed description is made to the present disclosure in conjunction with the accompanying drawings and embodiments. It should be understood that the specific embodiments described herein are merely explanative of the present disclosure, but not intended to limit the present disclosure.

Unless otherwise defined, all technical and scientific terms used herein have the same meanings of general understandings of persons skilled in the art of the present disclosure. Terms used in the description herein are only intended to describe the specific embodiments, but not to limit the present disclosure. The terms "and/or" include any and all combinations of one or multiple related listed items.

A lumen stent system of the present disclosure includes a lumen stent and a delivery system for delivering the lumen stent. The delivery system may implant the lumen stent into a lumen to form a new body fluid channel, for example, after being implanted into a blood vessel, the lumen stent may be a new blood flow channel.

Figure 1:
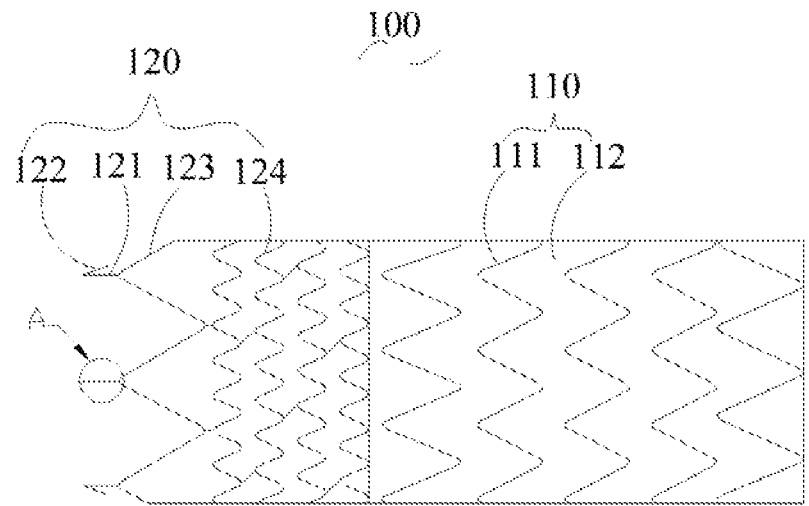
FIG. 1 is a structural schematic diagram of a lumen stent of the lumen stent system according to an embodiment of the present disclosure.
Figure 2:
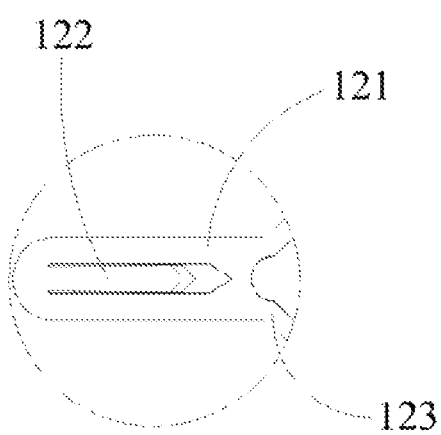
FIG. 2 is a local enlarged schematic diagram of section A in FIG. 1.

With reference to FIG. 1 and FIG. 2, a lumen stent 100 of an embodiment of the present disclosure includes a membrane covered stent 110 which is tubular and a bare stent 120, and the lumen stent 100 has a self-expansion characteristic.

The membrane covered stent 110 includes a plurality of waveform rings 111 formed by at least one woven wire, and a membrane 112 which covers the multiple waveform rings 111 and is used for fixing the multiple waveform rings 111. The membrane 112 may be made of terylene or e-PTFE. The woven wire may be a stainless steel wire or a nickel-titanium wire, or may be woven wires made by other biological materials. Each waveform ring 111 may include a plurality of V-shaped or Z-shaped waveform units or waveform units in other shapes.

The bare stent 120 includes a plurality of sheet-like connection parts 121. At least one barb 122 may be arranged on each connection part 121. One end of each barb 122 is arranged at the end portion of each connection part 121, and the end portion is far away from the membrane covered stent 110, and the other end of the barb 122 is an impending end which extends towards a direction close to the membrane covered stent 110. The barbs 122 and the connection parts 121 which the barbs 122 are arranged on form approximate V-shape. After the lumen stent 100 is completely released, the barbs 122 may puncture into a blood vessel wall so as to enable the lumen stent 100 to generate displacement resistance after being completely released.

Besides the connection parts 121, the bare stent 120 generally also includes a bare stent section which connects the connection parts 121 and the membrane covered stent 110. The bare stent section includes one or multiple circles of mutually connected waveform structures. The bare stent 120 may be designed into two forms, a long one and a short one, depending on the desired clinical application. Generally, the short bare stent includes one or two circles of waveform structures located between the connection parts 121 and the membrane covered stent 110, and the long bare stent includes at least two circles of waveform structures located between the connection parts 121 and the membrane covered stent 110. In this embodiment, the bare stent 120 is the long one, including a first waveform structure 123 connected with the connection parts 121, and a plurality of circles of second waveform structures 124 located between the first waveform structure 123 and the membrane covered stent 110. Each crest part of the first waveform structure 123 is connected with one connection part 121; and for the first waveform structure 123, its wave density is less than that of each second waveform structure 124, and its wave height is greater than that of each second waveform structure 124.

It can be understood that in other embodiments, there may be one or two circles of waveform structures connected with the connection parts 121 and the membrane covered stent 110. It also can be understood that in two adjacent circles of waveform structures, a perpendicular distance between the crest and the trough of one waveform structure, namely the wave height, may be greater than or equal to that of the other waveform structure.

The bare stent 120 may be formed by laser cutting, and of course, it also may be woven just like the membrane covered stent 110.

Figure 3:
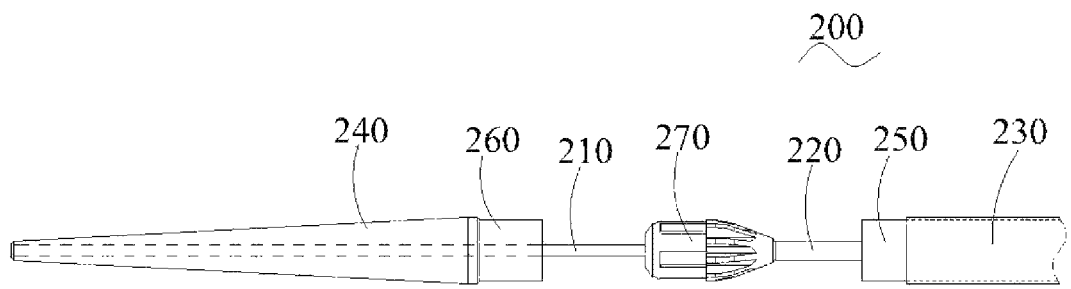
FIG. 3 is a structural schematic diagram of a delivery system of the lumen stent system according to an embodiment of the present disclosure.

With reference to FIG. 3, a delivery system 200 according to an embodiment of the present disclosure includes an inner core tube 210, an outer core tube 220 which surrounds the inner core tube 210 and may move axially relative to the inner core tube 210, and a sheath 230 which surrounds the outer core tube 220 and is used for taking the lumen stent 100 in.

In the interventional medical field, the end of the delivery system 200 which is close to an operator is called a proximal end, and the end far away from the operator is called a distal end.

An annular cavity is formed between the distal end of the sheath 230 and the outer core tube 220 of the delivery system 200. During the delivery process, the lumen stent 100 is radially compressed into the annular cavity.

In this embodiment, the delivery system 200 also includes a hollow end socket 240 which is located at the distal end of the inner core tube 210. The proximal end of the end socket 240 and the distal end of the inner core tube 210 are fixed together; and an inner cavity of the end socket 240 is communicated with a tube cavity of the inner core tube 210 to form a channel for wire guide. To be more specific, the proximal end of the end socket 240 and the distal end of the inner core tube 210 are burnt into a whole as an integrated structure.

In this embodiment, the delivery system 200 also includes a pushing tube 250 located between the outer core tube 220 and the sheath 230. The pushing tube 250 and the outer core tube 220 are coaxial, and are fixed together.

The delivery system 200 also includes a fixing cap 260 which is arranged at the proximal end of the end socket 240 and surrounds the inner core tube 210. The fixing cap 260 has a barrel structure with openings at two ends, and its side surface is a cylindrical surface; one end of the fixing cap 260 and the proximal end of the end socket 240 are fixedly connected, and are in smooth transition, so that scratching between the fixing cap 260 and other components may be avoided; the other end of the fixing cap 260 is an open end, which is used for taking in the connection parts 121 and the barbs 122 of the lumen stent 100 when the lumen stent 100 is placed into the delivery system 200.

Figure 4:
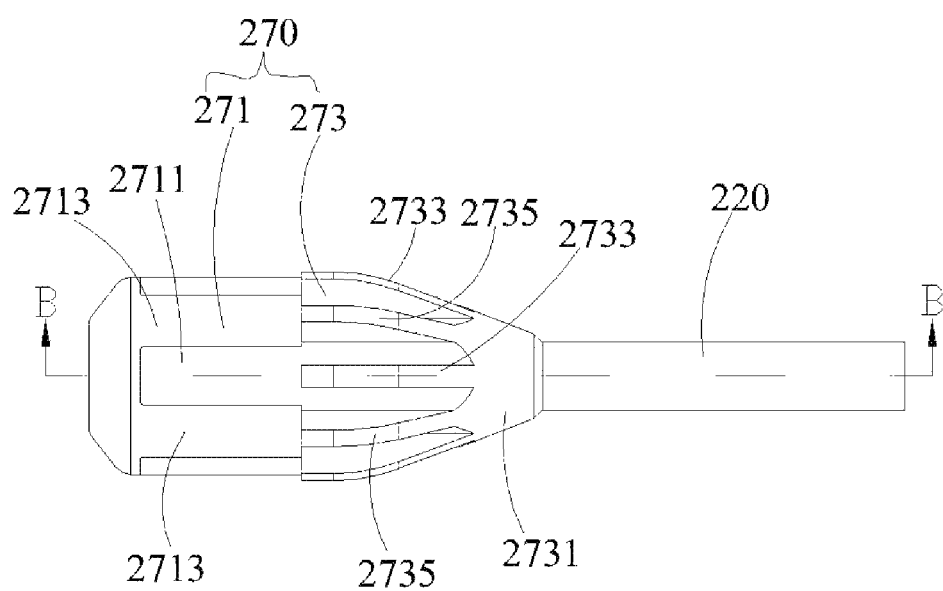
FIG. 4 is a structural schematic diagram of a fixing anchor and an outer core tube in FIG. 3.
Figure 5:
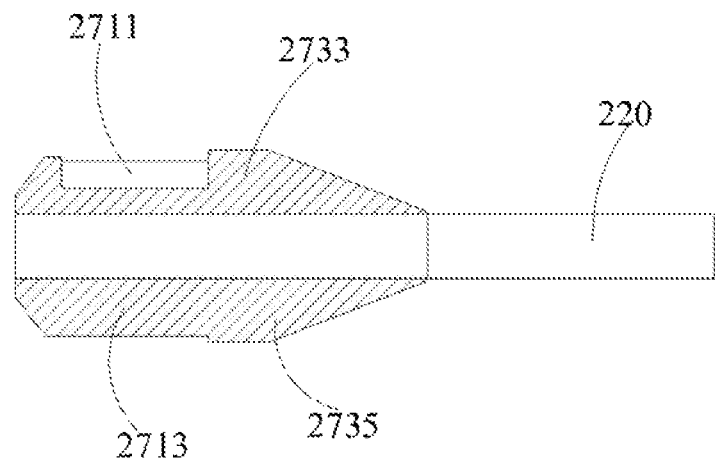
FIG. 5 is a sectional schematic diagram of the fixing anchor and the outer core tube in FIG. 4 along the line B-B.

With reference to FIGS. 4 to 5 in conjunction with FIGS. 1 to 3, the delivery system 200 also includes a hollow fixing anchor 270; the fixing anchor 270 is arranged on the outer side of the distal end of the outer core tube 220, and surrounds the outer core tube 220; the proximal end of the fixing anchor 270 and the distal end of the outer core tube 220 are fixed together, and an inner cavity of the fixing anchor 270 is communicated with the tube cavity of the outer core tube 220 to enable the fixing anchor 270 and the outer core tube 220 to surround the inner core tube 210 together and axially move relative to the inner core tube 210. The fixing anchor 270 is used for axially fixing the lumen stent 100, and cooperates with the fixing cap 260 to radially restrain the barbs 122.

In this embodiment, the fixing anchor 270 includes a hollow insertion part 271 located at the distal end and an abutment part 273 which is located at the proximal end and is connected with the insertion part 271.

The insertion part 271 has an approximately hollow cylindrical structure, and its outer diameter is slightly less than the inner diameter of the fixing cap 260, namely the insertion part 271 and the fixing cap 260 are in clearance fit to enable the insertion part 271 to be successfully inserted into the fixing cap 260. The insertion part 271 is inserted into the fixing cap 260, and cooperates with the fixing cap 260 to radially restrain the connection parts 121 and the barbs 122 of the lumen stent 100.

Part of the side surface of the insertion part 271 is sunken towards the inside of the insertion part 271 to form a plurality of positioning grooves 2711 penetrating through the proximal end surface of the insertion part 271. The positioning grooves 2711 are used for containing the connection parts 121 of the lumen stent 100; a separator 2713 is formed between every two adjacent positioning grooves 2711; the side, which is close to the abutment part 273 along a direction of the longitudinal central line of the insertion part 271, of each positioning groove 2711 is an open side, and the side, which is far away from the abutment part 273 along the direction of the longitudinal central line of the insertion part 271, of each positioning groove 2711 is a closed side; and the shape size of each positioning groove 2711 is slightly greater than that of each connection part 121, so that the connection parts 121 may be inserted from the open side of the positioning groove 2711, and is overall received in the positioning groove 2711.

In this embodiment, the multiple positioning grooves 2711 are uniformly arrayed on the side surface of the insertion part 271, and the shapes of the positioning grooves 2711 are approximately the same as those of the connection parts 121. It can be understood that the shapes of the positioning grooves 2711 may also be different from those of the connection parts 121 as long as the extending lengths of the positioning grooves 2711 along the direction of the longitudinal central line of the insertion part 271 are slightly greater than the lengths of the connection parts 121 to ensure that the connection parts 121 may be completely received in the positioning grooves 2711.

When the connection parts 121 of the lumen stent 100 are received in the positioning grooves 2711, and the insertion part 271 of the fixing anchor 270 is inserted into the fixing cap 260, the positioning grooves 2711 and the fixing cap 260 jointly achieve a radial restraining effect on the connection parts 121 and the barbs 122, so that the impending ends of the barbs 122 are kept in a compressed state. In addition, the closed sides of the positioning grooves 2711 may abut against the end portions of the connection parts 121, which are far away from the membrane covered stent 110, to prevent axial forward movement (which is a movement towards the distal end direction of the delivery system 200) of the lumen stent 100; and two adjacent separators 2713 separate adjacent connection parts 121 to prevent mutual interference of the adjacent connection parts 121.

The abutment part 273 includes a hollow carrier 2731, and a plurality of first position-limiting members 2733 with an elongated shape, and a plurality of second position-limiting members 2735 with an elongated shape, which are arranged on the side surface of the carrier 2731.

The carrier 2731 is connected with the insertion part 271, and a tube cavity of the carrier 2731 is communicated with that of the outer core tube 220. In this embodiment, the abutment part 273 and the insertion part 271 are integrally molded. It can be understood that the abutment part 273 may also be connected with the insertion part 271 by welding, adhesion and the like. The number of the first position-limiting members 2733 is equal to that of the second position-limiting members 2735, and the first position-limiting members 2733 and the second position-limiting members 2735 are alternately arrayed on the side surface of the carrier 2731, namely a second position-limiting piece 2735 is arranged between every two adjacent first position-limiting members 2733.

The structures of the first position-limiting members 2733 are substantially the same as those of the second position-limiting members 2735, and the first and the second position-limiting members are alternately arranged on the side surface of the distal end of the carrier 2731; and the distal end surfaces of the first and the second position-limiting members are coplanar with the distal end surface of the carrier 2731 and the proximal end surfaces of the separators 2713.

The cross section, which is perpendicular to the longitudinal central line of the outer core tube 220, of the distal end of the surface, far away from the carrier 2731, of each position-limiting piece in the first position-limiting members 2733 and the second position-limiting members 2735 is shaped like an arc section; the diameter of the arc section of each first position-limiting piece 2733 is the outer diameter of the distal end of the first position-limiting piece 2733; the diameter of the arc section of each second position-limiting piece 2735 is the outer diameter of the distal end of the second position-limiting piece 2735; and the outer diameters of the distal ends of the first and the second position-limiting members are all equal to the outer diameter of the proximal end of the fixing cap 260. Therefore, when the insertion part 271 is inserted into the fixing cap 260, the distal end surfaces of the first position-limiting members 2733 and the second position-limiting members 2735 all abut against the proximal end surface of the fixing cap 260, so that the lumen stent 100 may be restrained axially and radially under the common action of the fixing cap 260 and the fixing anchor 270; in addition, the cross section, which includes the longitudinal central line of the outer core tube 220, of the surface, far away from the carrier 2731, of each position-limiting piece in the first position-limiting members 2733 and the second position-limiting members 2735 has a curved shape, so that the fixing cap 260 is in smooth transition with the first position-limiting members 2733 and the second position-limiting members 2735, and the fixing cap 260 and the fixing anchor 270 are prevented from scratching the lumen stent 100 when it is withdrawn out of the body.

The lengthwise directions of the first position-limiting members 2733 and the second position-limiting members 2735 are all parallel to the longitudinal central line of the outer core tube 220, and the proximal end of each position-limiting piece in the first position-limiting members 2733 and the second position-limiting members 2735 extends towards the proximal end of the carrier 2731. The lengths of the first position-limiting members 2733 and the second position-limiting members 2735 are all less than the axial length of the carrier 2731. A distance from the surface, which is far away from the carrier 2731, of the distal end of each position-limiting piece in the first position-limiting members 2733 and the second position-limiting members 2735 to the longitudinal central line of the outer core tube 220, is longer than or equal to a distance from the surface, which is far away from the carrier 2731, of the proximal end of the corresponding position-limiting piece to the longitudinal central line of the outer core tube 220; the proximal end of each position-limiting piece in the first position-limiting members 2733 and the second position-limiting members 2735 extends to the proximal end of the carrier 2731; the proximal end of the carrier 2731 extends to the outer core tube 220, and the outer surfaces of the proximal ends of the first position-limiting members 2733 and the second position-limiting members 2735, the proximal end of the carrier 2731 and the outer core tube 220 are in a smooth conical transition so that the proximal end of the abutment part 273 has a substantially smooth conical contour, which prevents the abutment part 273 from scratching the lumen stent 100 when the fixing anchor 270 is withdrawn out of the body, and improves the operation safety.

The first position-limiting members 2733 are distributed on the outer surface of the carrier 2731 in an equal spaced apart manner along the circumferential direction of the carrier 2731, and the distal end of each first position-limiting piece 2733 is arranged to correspond to the open side of a positioning groove 2711 of the insertion part 271; that is, the number of the first position-limiting members 2733 and the number of the multiple positioning grooves 2711 are equal, and both are equal to the number of the connection parts 121 of the lumen stent 100.

Therefore, when the connection parts 121 are received in the positioning grooves 2711, the first position-limiting members 2733 may be clamped in a crest part of the first waveform structure 123 of the lumen stent 100 to prevent axial backward movement (which is a movement towards the proximal end direction of the delivery system 200) of the lumen stent 100 before it is completely released and expanded.

The second position-limiting members 2735 are distributed on the outer surface of the carrier 2731 in an equal spaced-apart manner along the circumferential direction of the carrier 2731, and a first position-limiting piece 2733 is arranged between every two adjacent second position-limiting members 2735. The distal end of each second position-limiting piece 2735 is arranged to correspond to the proximal end of a separator 2713 of the insertion part 271, and the distal end surfaces of the second position-limiting members 2735 are coplanar with the proximal end surfaces of the separators 2713.

The width of each positioning groove 2711 along the circumferential direction of the insertion part 271 is greater than that of each first position-limiting piece 2733, which corresponds to the corresponding positioning groove 2711, along the circumferential direction of the abutment part 273, and less than a distance between two second position-limiting members 2735 adjacent to the left and right of the first position-limiting piece 2733 along the circumferential direction of the abutment part 273. In other words, the width of the separators 2713 along the circumferential direction of the insertion part 271 is greater than the second position-limiting members 2735, which correspond to the corresponding separators 2713, along the circumferential direction of the abutment part 273. Each positioning groove 2711 and the corresponding first position-limiting piece 2733, and two second position-limiting members 2735 adjacent to the left and right of the corresponding first position-limiting piece 2733, jointly form a substantially U-shaped groove.

Figure 6:
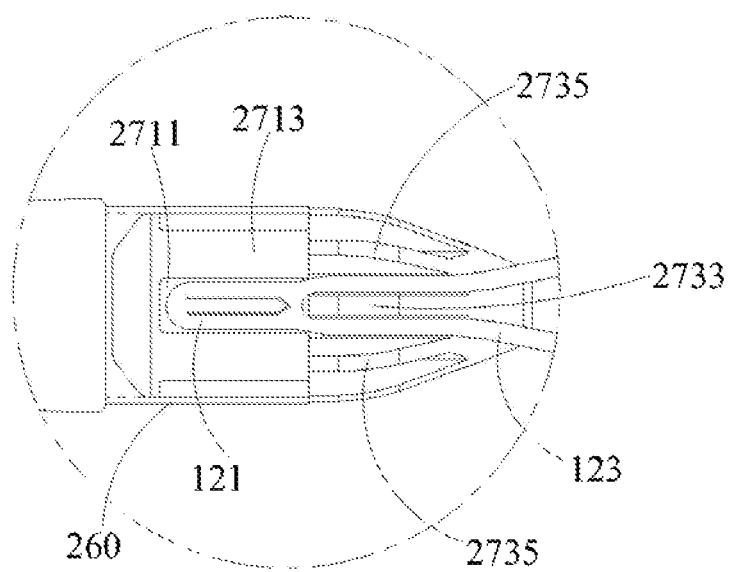
FIG. 6 is a schematic diagram showing the cooperation of a fixing cap, a fixing anchor and connection parts of an embodiment of the present disclosure.

Referring also to FIG. 6 (to clearly show an internal structure, the fixing cap 260 is shown to be transparent in the figure), in a process of assembling the bare stent 120 of the lumen stent 100 into the fixing anchor 270, the connection parts 121 are received in the positioning grooves 2711 of the insertion part 271, and are inserted into the fixing cap 260 together with the insertion part 271; two adjacent separators 2713 separate adjacent connection parts 121 to prevent mutual interference of the adjacent connection parts 121; the crest parts of the first waveform structure 123 connected with the connection parts 121 are clamped at the first position-limiting members 2733, and two adjacent second position-limiting members 2735 separate two adjacent crest parts of the first waveform structure 123 to prevent mutual interference of the two adjacent crest parts; and in addition, the first position-limiting piece 2733 between two adjacent second position-limiting pieces 2735 separates two sides of a crest part to prevent mutual interference of the two sides of the same crest part.

A further description will be made below to a working process of the lumen stent system of the present disclosure in conjunction with the accompanying drawings.

Figure 7:
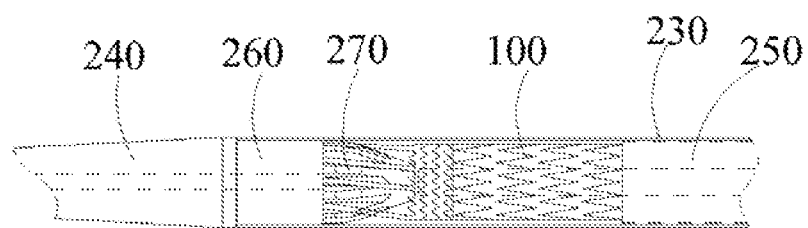
FIG. 7 is a schematic diagram of a lumen stent system according to an embodiment of the present disclosure, with the lumen stent compressed in a delivery system.

First, the entire lumen stent 100 is placed into the annular cavity formed by the outer core tube 220 and the sheath 230 of the delivery system 200 after being subjected to radial compression, as shown in FIG. 7 (to clearly show an internal structure, the sheath 230 is shown to be transparent in the figure). At the moment, the distal end of the sheath 230 is positioned close to the proximal end of the end socket 240, and is even in contact with the proximal end; the fixing cap 260, the inner core tube 210, the fixing anchor 270, the outer core tube 220 and the pushing tube 250 are all located in the sheath 230. With the connection parts 121 and the barbs 122 which are received in the positioning grooves 2711, the insertion part 271 of the fixing anchor 270 is inserted into the fixing cap 260; the first position-limiting members 2733 of the fixing anchor 270 are embedded into the crest parts of the first waveform structure 123, and the second position-limiting members 2735 separate two adjacent crest parts. The membrane covered stent 110 of the lumen stent 100 is located on the outer side of the outer core tube. A guide wire (not shown) is introduced through an incision in the iliac artery, and the distal end of the guide wire is delivered to a diseased position, thus building a delivery track. The delivery system 200 and the lumen stent 100 located in the delivery system 200 are pushed to the diseased position together along the guide wire.

During the process of delivering and positioning the lumen stent 100, as the distal end surfaces of the first position-limiting members 2733 and the second position-limiting members 2735 of the fixing anchor 270 are aligned with and abut against the proximal end surface of the fixing cap 260, the fixing anchor 270 and the fixing cap 260 are kept relatively static, so that under their common action, axial and radial restraint of the lumen stent 100 may be achieved, and the lumen stent 100 will not move relative to the delivery system 200 before reaching a predetermined diseased position.

Figure 8:
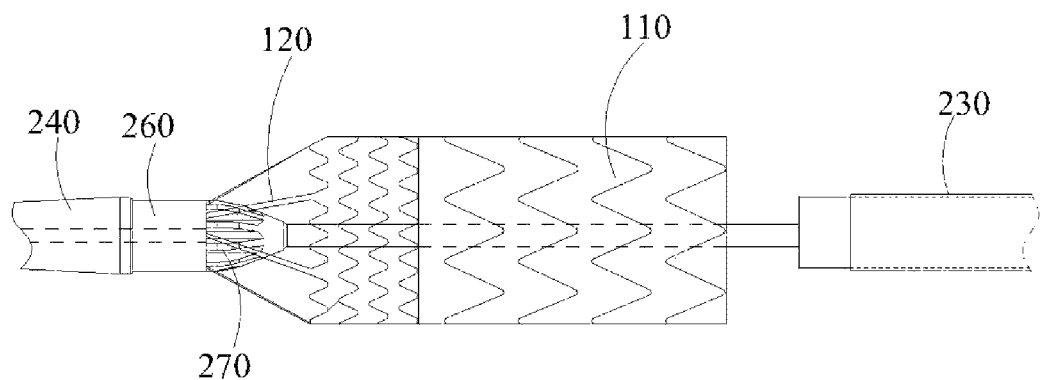
FIG. 8 is a schematic diagram of a lumen stent system according to an embodiment of the present disclosure, with the lumen stent in a half-released state.

When the lumen stent 100 reaches the diseased position, the sheath 230 is pulled towards the proximal end, and then is withdrawn to slowly separate from the end socket 240; and due to the action of the fixing cap 260 and the fixing anchor 270, the bare stent 120 of the lumen stent 100 is still in a compressed state, and not released. When the sheath 230 is withdrawn to slowly expose the outer core tube 220, the membrane covered stent 110 of the lumen stent 100 is released step by step as restraining force of the sheath 230 slowly disappears. In addition, during this process, as the sheath 230 and the lumen stent 100 have a certain friction force, the lumen stent 100 would have an axial backward movement trend during the withdrawal of the sheath 230. However, as the fixing anchor 270 of the delivery system 200 limits backward movement of the lumen stent 100, the fixing cap 260, the fixing anchor 270 and the lumen stent 100 are kept relatively static; even if during the process of releasing the membrane covered stent 110 of the lumen stent 100, the bare stent 120 of the lumen stent 100 is also in the compressed state the entire time instead of being expanded in advance, so that the risk of displacement of the lumen stent 100 due to early expansion is avoided. When the membrane covered stent 110 of the lumen stent 100 is completely released, it is as shown in FIG. 8.

To further completely release the lumen stent 100, the inner core tube 210 is pushed to move towards the distal end, and drives the end socket 240 and the fixing cap 260 to axially move forward, so that the heads of the barbs 122 of the lumen stent 100 are slowly separated from the fixing cap 260. As a certain friction force exists between the fixing cap 260 and the barbs 122 of the lumen stent 100, the lumen stent 100 has an axial forward movement trend along with the end socket 240 under the action of the friction force. However, as the closed sides of the positioning grooves 2711 of the insertion part 271 of the fixing anchor 270 abut against the end portions, which are far away from the membrane covered stent 110, of the side barb supporting structures 121, and may limit the axial forward movement of the lumen stent 100, the risk that the lumen stent 100 moves along with the movement of the end socket 240 is avoided.

Figure 9:
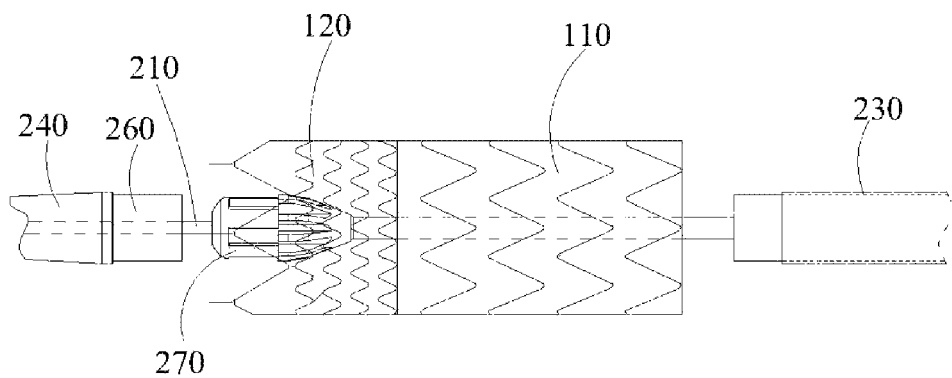
FIG. 9 is a schematic diagram of a lumen stent system according to an embodiment of the present disclosure, with the lumen stent fully released.

When the connection parts 121 of the lumen stent 100 are completely separated from the fixing cap 260, the radial restraining force on the connection parts 121 of the lumen stent 100 disappears; under the action of radial self-expansion force of the lumen stent 100, the connection parts 121 are separated from the positioning grooves 2711 of the fixing anchor 270, and at that moment, the lumen stent 100 is completely separated from the delivery system 200, and is expanded and secured to the lumen wall. The whole lumen stent 100 is therefore completely released, which is as shown in FIG. 9.

Figure 10:
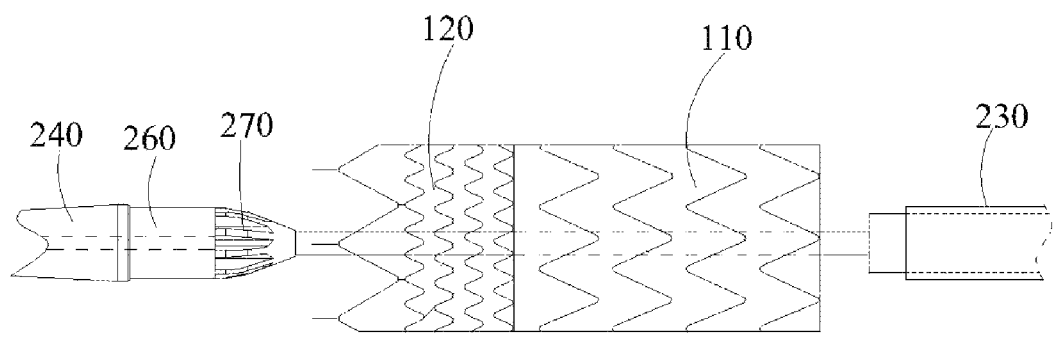
FIG. 10 is a schematic diagram of a lumen stent system according to an embodiment of the present disclosure, with the delivery system being withdrawn.

Finally, as shown in FIG. 10, the inner core tube 210 is pulled to drive the end socket 240 and the fixing cap 260 to axially move proximally to enable the fixing cap 260 and the fixing anchor 270 to be joined; that is, the insertion part 271 of the fixing anchor 270 is inserted into the fixing cap 260; and the entire delivery system 200 and the guide wire are continuously pulled proximally till they are withdrawn out of the body.

Figure 11:
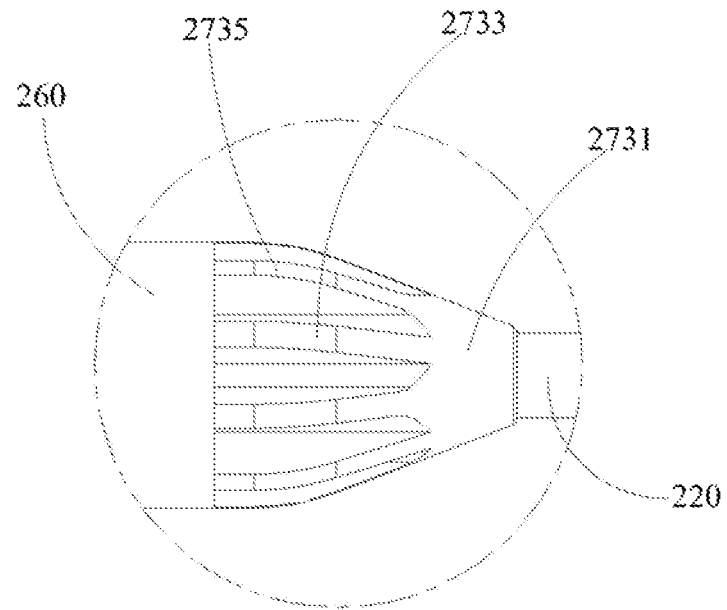
FIG. 11 is a schematic diagram showing the cooperation of the fixing cap and the fixing anchor in FIG. 10.

Referring also to FIG. 11, as the side surface of the fixing cap 260 and the outer surfaces of the first position-limiting members 2733 and the second position-limiting members 2735 are in smooth transition, and the proximal end of the abutment part 273 of the fixing anchor 270 has the smooth conical contour, the possibility of scratching between the outer surfaces of the fixing anchor 270 and the fixing cap 260 and the lumen stent 100 during withdrawal of the entire delivery system 200 may be reduced.

Figure 12:
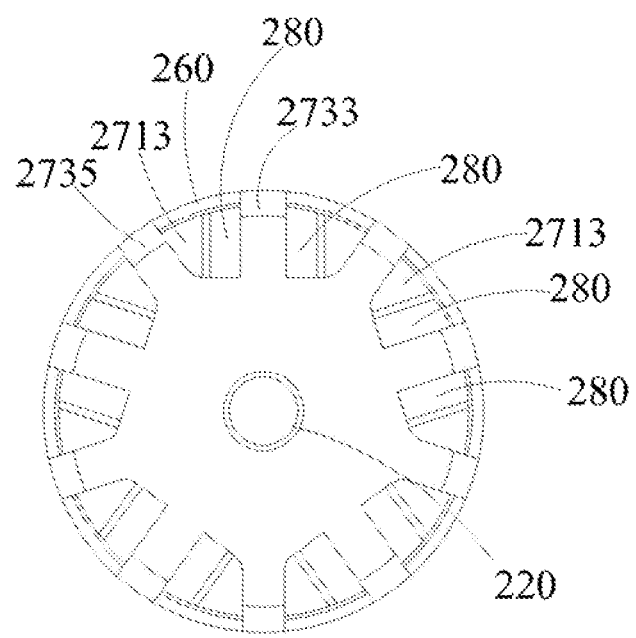
FIG. 12 is a left view of the schematic diagram of the cooperation of the fixing cap and the fixing anchor in FIG. 11.

With reference to FIG. 12, during the withdrawal process, after the fixing cap 260 and the fixing anchor 270 are joined, a plurality of small holes 280 are formed in a plane, where the proximal end surface of the fixing cap 260 is located, by the side surface of the fixing cap 260 together with the multiple separators 2713, the first position-limiting members 2733 and the carrier 2731; each small hole 280 is jointly formed by one separator 2713, one first position-limiting piece 2733 adjacent to the separator 2713, the side surface of the fixing cap 260 and the carrier 2731. The first position-limiting members 2733, the carrier 2731 and the separators 2713 divide the proximal end surface of the fixing cap 260 into the multiple small holes 280, so as to prevent the delivery system 200 from hooking the released lumen stent 100 during withdrawal. Further, the shape size of each positioning groove 2711 is slightly greater than that of each connection part 121, and each first position-limiting piece 2733 also has a certain width along the circumferential direction of the abutment part 273, so that the width of each small hole 280 along the circumferential direction of the abutment part 273 is less than half of the width of each positioning groove 2711 along the circumferential direction of the insertion part 271. Therefore, the width of each small hole 280 along the circumferential direction of the abutment part 273 is less than that of the end portion of each connection part 121 along the circumferential direction of the lumen stent 100, and much less than that of each crest part of the first waveform structure 123 and the second waveform structures 124 in the bare stent 120 of the lumen stent 100 along the circumferential direction of the lumen stent 100 and that of each crest part of each waveform ring 111 in the membrane covered stent 110 along the circumferential direction of the lumen stent 100; and therefore, the end portions of the connection parts 121 and these crest parts cannot be inserted or clamped into the small holes 280, so that the entire delivery system 200 may be further successfully and safely withdrawn from the body after the lumen stent 100 is completely released.

Figure 13:
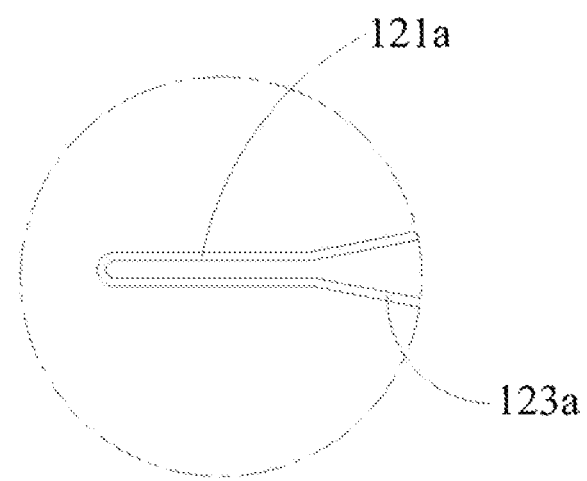
FIG. 13 is a structural schematic diagram of a connection part of a lumen stent of the lumen stent system according to another embodiment of the present disclosure.

It can be understood that it is possible for the barbs 122 to not be arranged on the connection parts 121 of the lumen stent 100. It also can be understood that the connection parts 121 may also be of other structures. With reference to FIG. 13, the connection parts are different from those in the above-mentioned embodiments in that a first waveform structure 123a is disconnected at the crest part; the connection part 121a has a U-shaped open-loop structure with an opening in one side; two ends of the open side of each connection part 121a are respectively connected with two ends of each disconnected portion of the first waveform structure 123a, so that the crest part of the first waveform structure 123a is communicated with the connection part 121a; and barbs also may be arranged on the connection parts 121a.

Figure 14:
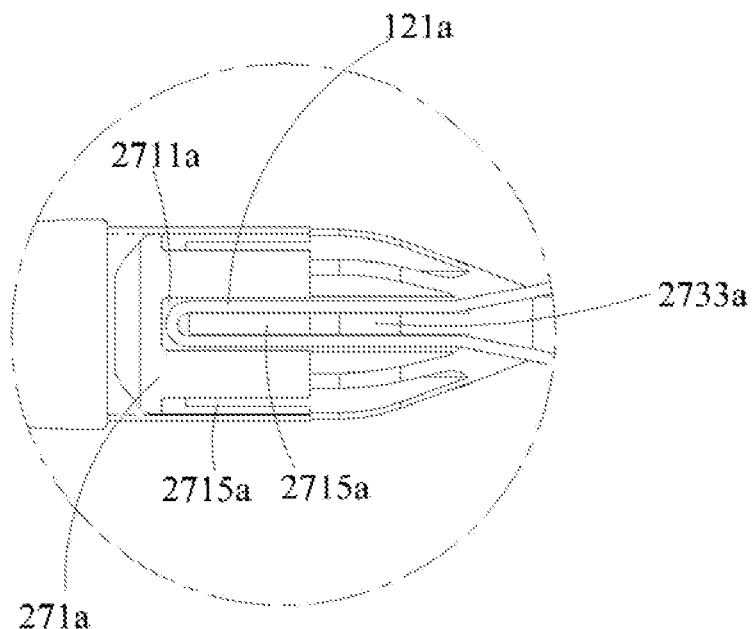
FIG. 14 is a schematic diagram showing the cooperation between the connection part in FIG. 13 and a fixing anchor and a fixing cap according to another embodiment of the present disclosure.

It can be understood that according to structural changes of the connection parts, the structure of the fixing anchor may also change corresponding to a clinical requirement. With reference to FIG. 14, when the structures of the connection parts are the same as those of the connection parts 121a in FIG. 13, the structure of a fixing anchor is substantially the same as that of the fixing anchor 270, but what is different is that the structure of the insertion part 271a is slightly different from that of the insertion part 271 in the above embodiment. To be more specific, axial backward movement limiting members 2715a are arranged in positioning grooves 2711a of the insertion part 271a; each axial backward movement limiting piece 2715a is spaced from the side, which is perpendicular to the circumferential direction of the insertion part 271, of each positioning groove 2711a, and protrudes from the groove bottom, which is parallel to the circumferential direction of the insertion part 271, of each positioning groove 2711a; and the axial backward movement limiting members 2715a may be inserted into the fixing cap together with the insertion part 271a. In this embodiment, the axial backward movement limiting members 2715a extend towards first position-limiting members 2733a of the abutment part along the longitudinal central line of the fixing anchor, and are connected with the first position-limiting members 2733a. When a lumen stent is loaded into a delivery system, the connection parts 121a of the lumen stent are received in the positioning grooves 2711a, and are clamped on the axial backward movement limiting members 2715a.

Therefore, even if the connection parts 121a are communicated with the first waveform structure 123a, the connection parts 121a may still not be clamped at the first position-limiting members 2733a to prevent axial backward movement of the lumen stent; but the arrangement of the axial backward movement limiting members 2715a in the positioning grooves 2711a enables the connection parts 121a to be clamped at the axial backward movement limiting members 2715a, so as accomplish the objective of preventing the axial backward movement of the lumen stent.

Figure 15:
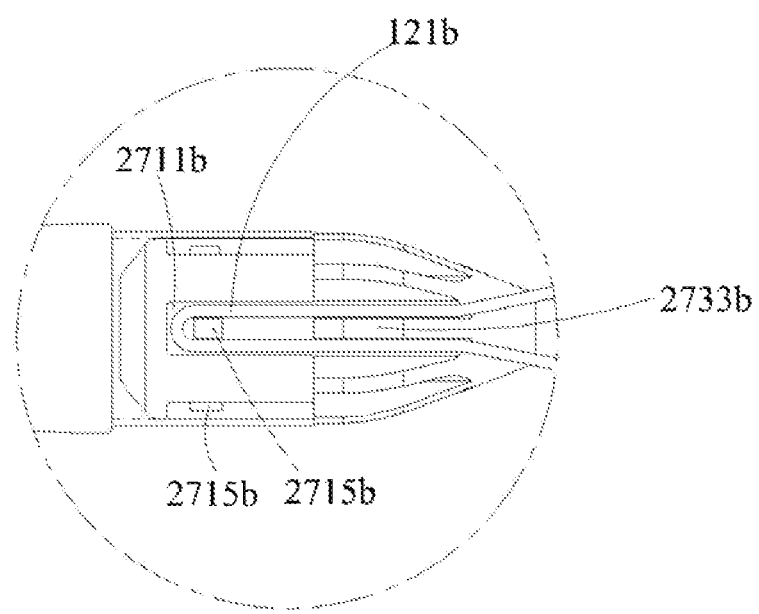
FIG. 15 is a schematic diagram showing cooperation between the connection part in FIG. 13 and a fixing anchor and a fixing cap according to another embodiment of the present disclosure.

It can be understood that the axial backward movement limiting members also may not be connected with the first position-limiting members of the abutment part. With reference to FIG. 15, axial backward movement limiting members 2715b are square blocks arranged in a convex manner at the groove bottoms of positioning grooves 2711a; a certain distance exists between each axial backward movement limiting piece 2715b and the side, which is perpendicular to the circumferential direction of the insertion part 271, of each positioning groove 2711a, and a certain distance also exists between each axial backward movement limiting piece 2715b and each first position-limiting piece 2733b. Connection parts 121b may still be received in the positioning grooves 2711b, and clamped in the axial backward movement limiting members 2715b to prevent axial backward movement of the lumen stent.

It can be understood that the axial backward movement limiting members may also be in other shapes, but not limited to the shapes listed above as long as the axial backward movement limiting members can cooperate with the connection parts to accomplish the objective of preventing the axial backward movement of the lumen stent.

All technical features of the above-mentioned embodiments may be combined randomly. To make the description simple and clear, not all possible combinations of all the technical features in the above-mentioned embodiments are described, but the combinations of these technical features shall fall within the scope described in the specification as long as no contradictions exist in them.

The above-mentioned embodiments are merely expressive of several implementation modes of the present disclosure, and their descriptions are specific and detailed, but are not understood as limitations to the scope of the patent according to the present disclosure. It should be noted that ordinary persons skilled in the art further can make a plurality of deformations and improvements which shall all fall within the scope of protection of the present disclosure without departing from the concept of the present disclosure. Therefore, for the scope of protection of the patent according to the present disclosure, the following claims shall prevail.

The invention claimed is:

1. A lumen stent system, comprising:
a lumen stent comprising a bare stent that comprises a plurality of waveform rings that includes a first waveform structure that has a plurality of crest parts, the bare stent also comprising a plurality of connection parts, with each crest part of the first waveform structure connected with one of the plurality of connection parts, and wherein each connection part has an end portion that has a width;
a delivery system for delivering the lumen stent, comprising:
a barrel-shaped fixing cap having a proximal end with an opening, and a side surface;
a fixing anchor comprising a hollow insertion part and an abutment part connected with the insertion part;
wherein the insertion part has a proximal end and a side surface, with a plurality of positioning grooves sunken from the side surface and with adjacent positioning grooves separated by alternating raised separators, and with each positioning groove having an opened proximal end that is adjacent the abutment part;
wherein the abutment part has a carrier that has a side surface, and a plurality of first position-limiting members arranged on the side surface of the carrier, each first position-limiting member having a distal end that is arranged to be positioned adjacent an opened proximal end of a positioning groove;
wherein the distal end of each first position-limiting member has a distal end outer surface, and each separator has a proximal end that has a proximal end outer surface, with the distal end outer surface of each first position-limiting member being co-planar with the proximal end outer surface of an adjacent separator; and
when the fixing anchor and the fixing cap are joined, the insertion part is inserted through the opening into the fixing cap, and the distal end of the first position-limiting members abut against the proximal end of the fixing cap;
wherein the fixing anchor and the lumen stent each has a circumferential direction;
wherein when the fixing anchor and the fixing cap are joined: (i) the connection parts are received in the positioning grooves, and (ii) at least one hole is formed by each separator, each first position-limiting member adjacent to each corresponding separator, the fixing cap and the carrier;
each hole having a width and being located where the proximal end of the fixing cap is located; and
wherein the width of each hole along the circumferential direction of the fixing anchor is less than the width of the end portion of each connection part along the circumferential direction of the lumen stent; and
wherein when the fixing anchor and the fixing cap are joined, the first position-limiting members are clamped with the crest parts of the first waveform structure.

2. The system according to claim 1, wherein each separator has a proximal end and the abutment part also comprises a plurality of second position-limiting members, each second position-limiting member having a distal end;
wherein the number of the second position-limiting members is equal to that of the first position-limiting members;
wherein the second position-limiting members and the first position-limiting members are alternately arrayed on the side surface of the carrier;
wherein each second position-limiting member is arranged to correspond to a separator, and the distal end of each second position-limiting member abuts against the proximal end of each corresponding separator.

3. The system according to claim 2, wherein each separator and each second position-limiting member has a width, and the insertion part and the abutment part each has a circumferential direction;
wherein the width of the separators along the circumferential direction of the insertion part is greater than the width of the corresponding second position-limiting members along the circumferential direction of the abutment part.

4. The system according to claim 2, wherein the fixing anchor has a longitudinal central line, the proximal end of the fixing cap has an outer diameter, and each first position-limiting member and each second position-limiting member has a cross-section which is perpendicular to the longitudinal central line of the fixing anchor;
and wherein the cross sections of each first position-limiting member and each second position-limiting member are shaped like an arc section, where each arc section has a diameter, and wherein the diameters of the arc sections are equal to the outer diameter of the proximal end of the fixing cap.

5. The system according to claim 2, wherein the first position-limiting members and the second position-limiting members each has a length, a proximal end and a lengthwise direction, the carrier has an axial length and a proximal end, and the fixing anchor has a longitudinal central line;
 wherein the lengthwise directions of the first position-limiting members and the second position-limiting members are all parallel to the longitudinal central line of the fixing anchor, and the proximal ends of the first position-limiting members and the second position-limiting members all extend towards the proximal end of the carrier;
 wherein the lengths of the first position-limiting members and the second position-limiting members are all less than the axial length of the carrier; and
 wherein the proximal end of the carrier has an outer surface, and the proximal end of each first position-limiting member and each second position-limiting member has an outer surface, with the outer surfaces of the proximal ends of each first position-limiting member and each second position-limiting member being in conical smooth transition with the outer surface of the proximal end of the carrier.

6. The system according to claim 1, wherein each positioning groove has a closed distal end.

7. The system according to claim 1, wherein the delivery system further comprises:
 an inner core tube having a distal end,
 an end socket having a proximal end, the end socket arranged at the distal end of the inner core tube, and
 an outer core tube which surrounds the inner core tube and moves axially relative to the inner core tube, the outer core tube having a distal end;
 wherein the fixing cap is arranged at the proximal end of the end socket, and surrounds the inner core tube;
 the fixing anchor is arranged at the distal end of the outer core tube, and surrounds the outer core tube; and
 the fixing cap is closer to the end socket than the fixing anchor.

8. The system according to claim 7, wherein the outer core tube has an outer surface and the carrier has a proximal end which has an outer surface, the proximal end of the carrier extends to the outer core tube, and the outer surface of the proximal end of the carrier is in conical transition with the outer surface of the outer core tube.

9. The system according to claim 1, wherein barbs are arranged on the connection parts.

10. A lumen stent system, comprising:
 a lumen stent comprising a bare stent that comprises waveform rings and a plurality of connection parts connected with the waveform rings, wherein each connection part has an end portion that has a width;
 a delivery system for delivering the lumen stent, comprising:
  a barrel-shaped fixing cap having a proximal end with an opening, and a side surface;
  a fixing anchor comprising a hollow insertion part and an abutment part connected with the insertion part;
  wherein the insertion part has a proximal end and a side surface, with a plurality of positioning grooves sunken from the side surface and with adjacent positioning grooves separated by alternating raised separators, and with each positioning groove having an opened proximal end that is adjacent the abutment part;
  wherein the abutment part has a carrier that has a side surface, and a plurality of first position-limiting members arranged on the side surface of the carrier, each first position-limiting member having a distal end that is arranged to be positioned adjacent an opened proximal end of a positioning groove;
  wherein the distal end of each first position-limiting member has a distal end outer surface, and each separator has a proximal end that has a proximal end outer surface, with the distal end outer surface of each first position-limiting member being co-planar with the proximal end outer surface of an adjacent separator; and
  when the fixing anchor and the fixing cap are joined, the insertion part is inserted through the opening into the fixing cap, and the distal end of the first position-limiting members abut against the proximal end of the fixing cap;
 wherein the fixing anchor and the lumen stent each has a circumferential direction;
 wherein when the fixing anchor and the fixing cap are joined: (i) the connection parts are received in the positioning grooves, and (ii) at least one hole is formed by each separator, each first position-limiting member adjacent to each corresponding separator, the fixing cap and the carrier;
 each hole having a width and being located where the proximal end of the fixing cap is located; and
 wherein the width of each hole along the circumferential direction of the fixing anchor is less than the width of the end portion of each connection part along the circumferential direction of the lumen stent; and
 wherein:
 the connection part has a U-shaped open-loop structure with an opening in one side, the one side having two ends; the waveform ring has crest part, and the waveform ring is disconnected at the crest part at a disconnected position; two ends of the open side of each connection part are respectively connected with two ends of each disconnected position of each waveform ring;
 the insertion part has a circumferential direction, and each positioning groove has a groove bottom which is parallel to the circumferential direction of the insertion part, and a side which is perpendicular to the circumferential direction of the insertion part;
 axial backward movement limiting members are arranged in the positioning grooves of the insertion part, with each axial backward movement limiting piece spaced from the side of each positioning groove which is perpendicular to the circumferential direction of the insertion part, and protruding from the groove bottom of each positioning groove;
 the connection parts are retained in the positioning grooves; and
 the connection parts are clamped with the axial backward movement limiting members.

11. The system according to claim 10, wherein the fixing anchor has a longitudinal central line; and wherein the axial backward movement limiting members extend towards the first position-limiting members along the longitudinal central line of the fixing anchor, and are connected with the first position-limiting members.

12. The system according to claim 10, wherein each positioning groove has a closed distal end.

13. The system according to claim 10, wherein the delivery system further comprises:
an inner core tube having a distal end,
an end socket having a proximal end, the end socket arranged at the distal end of the inner core tube, and
an outer core tube which surrounds the inner core tube and moves axially relative to the inner core tube, the outer core tube having a distal end;
wherein the fixing cap is arranged at the proximal end of the end socket, and surrounds the inner core tube;
the fixing anchor is arranged at the distal end of the outer core tube, and surrounds the outer core tube; and
the fixing cap is closer to the end socket than the fixing anchor.

14. The system according to claim 10, wherein the outer core tube has an outer surface and the carrier has a proximal end which has an outer surface, the proximal end of the carrier extends to the outer core tube, and the outer surface of the proximal end of the carrier is in conical transition with the outer surface of the outer core tube.

15. The system according to claim 10, wherein each separator has a proximal end and the abutment part also comprises a plurality of second position-limiting members, each second position-limiting member having a distal end;
wherein the number of the second position-limiting members is equal to that of the first position-limiting members;
wherein the second position-limiting members and the first position-limiting members are alternately arrayed on the side surface of the carrier;
wherein each second position-limiting member is arranged to correspond to a separator, and the distal end of each second position-limiting member abuts against the proximal end of each corresponding separator.

16. The system according to claim 15, wherein each separator and each second position-limiting member has a width, and the insertion part and the abutment part each has a circumferential direction;
wherein the width of the separators along the circumferential direction of the insertion part is greater than the width of the corresponding second position-limiting members along the circumferential direction of the abutment part.

17. The system according to claim 15, wherein the fixing anchor has a longitudinal central line, the proximal end of the fixing cap has an outer diameter, and each first position-limiting member and each second position-limiting member has a cross-section which is perpendicular to the longitudinal central line of the fixing anchor;
and wherein the cross sections of each first position-limiting member and each second position-limiting member are shaped like an arc section, where each arc section has a diameter, and wherein the diameters of the arc sections are equal to the outer diameter of the proximal end of the fixing cap.

18. The system according to claim 17, wherein the first position-limiting members and the second position-limiting members each has a length, a proximal end and a lengthwise direction, the carrier has an axial length and a proximal end, and the fixing anchor has a longitudinal central line;
wherein the lengthwise directions of the first position-limiting members and the second position-limiting members are all parallel to the longitudinal central line of the fixing anchor, and the proximal ends of the first position-limiting members and the second position-limiting members all extend towards the proximal end of the carrier;
wherein the lengths of the first position-limiting members and the second position-limiting members are all less than the axial length of the carrier; and
wherein the proximal end of the carrier has an outer surface, and the proximal end of each first position-limiting member and each second position-limiting member has an outer surface, with the outer surfaces of the proximal ends of each first position-limiting member and each second position-limiting member being in conical smooth
transition with the outer surface of the proximal end of the carrier.

19. The system according to claim 10, wherein barbs are arranged on the connection parts.

\* \* \* \* \*